(12) United States Patent
Huang

(10) Patent No.: US 7,439,474 B2
(45) Date of Patent: Oct. 21, 2008

(54) LOW VOLTAGE AND HIGH PERFORMANCE CLIMATE CONTROL PAD FOR SKIN SURFACE

(76) Inventor: Charlie Huang, 7121 Stonewood Dr., Huntington Beach, CA (US) 92647

( * ) Notice: Subject to any disclaimer, the term of this patent is extended or adjusted under 35 U.S.C. 154(b) by 567 days.

(21) Appl. No.: 11/112,404

(22) Filed: Apr. 21, 2005

(65) Prior Publication Data

US 2006/0241730 A1    Oct. 26, 2006

(51) Int. Cl.
*H05B 3/34* (2006.01)
*A61F 7/00* (2006.01)

(52) U.S. Cl. .................... 219/549; 219/211; 219/212; 219/217; 219/527; 219/528; 219/529; 607/98

(58) Field of Classification Search ........... 219/211–12, 219/217, 527–9, 549; 607/98
See application file for complete search history.

(56) References Cited

U.S. PATENT DOCUMENTS 2,612,585 A * 9/1952 McCann ............... 392/435
7,205,510 B2 * 4/2007 Howick ............... 219/529

* cited by examiner

*Primary Examiner*—Shawntina Fuqua
(74) *Attorney, Agent, or Firm*—Raymond Y. Chan; David and Raymond Patent Firm

(57) ABSTRACT

A climate control pad includes a pad body having a climate treating surface and an air circulating circuit formed thereon for preserving a volume of air within the air circulating circuit in a circulating manner, and a heat generating element, which is a fiber heating wire, disposed in the air circulating circuit for generating heat to increase the temperature of the air within the air circulating circuit so as to evenly distribute the heat from the heat generating element on the climate treating surface of the pad body. In addition, the pad body is adapted to incorporate with a cooling source to provide a cooling air towards the climate treating surface of the pad body.

15 Claims, 8 Drawing Sheets

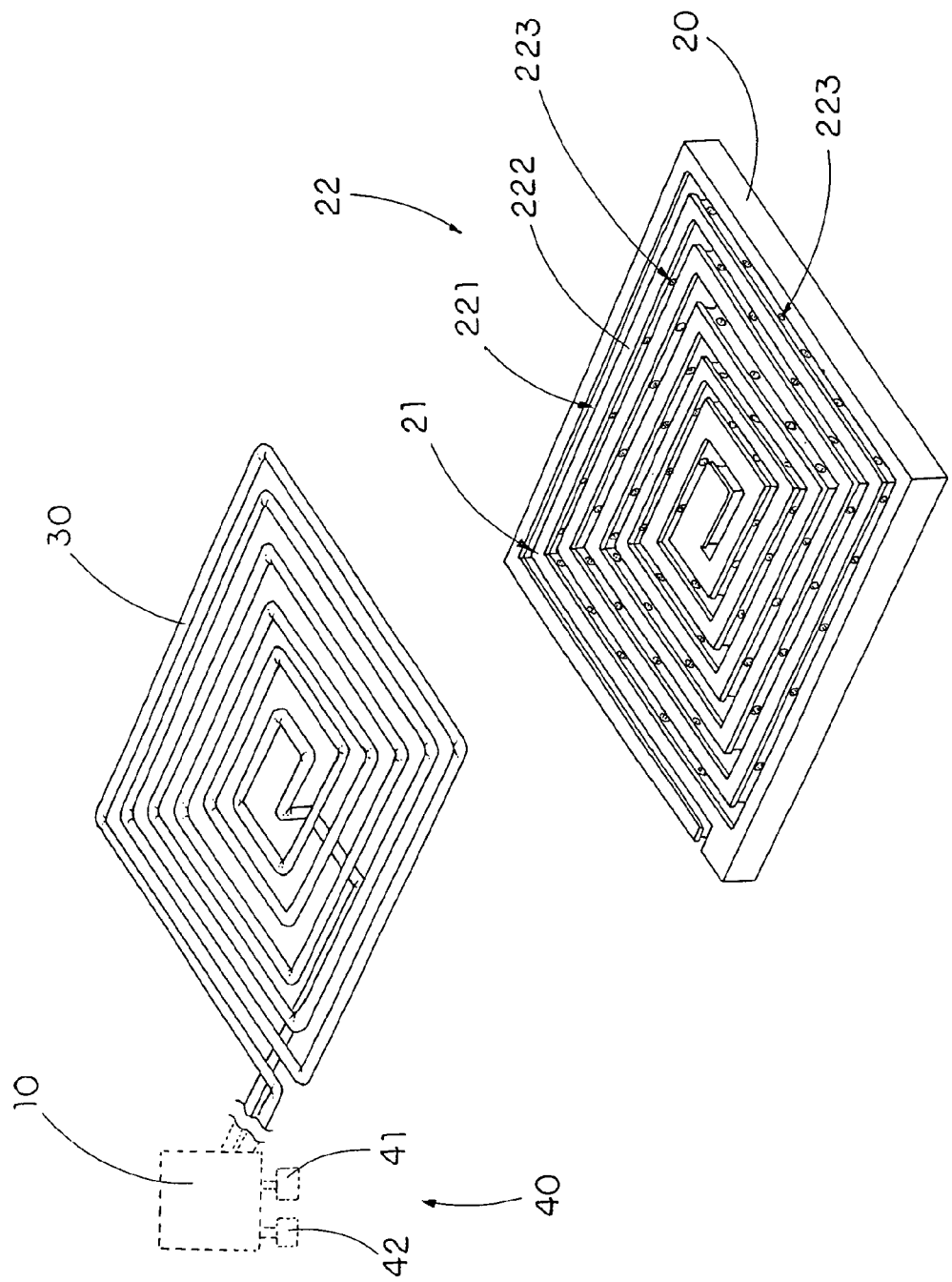

LOW VOLTAGE AND HIGH PERFORMANCE CLIMATE CONTROL PAD FOR SKIN SURFACE

BACKGROUND OF THE PRESENT INVENTION

1. Field of Invention

The present invention relates to a heat treating pad for a skin surface, and more particularly to a low voltage and high performance climate control pad for the skin surface, wherein an air circulating circuit is formed on a pad body for a heat generating element disposing thereon so as to provide an even heat/cold treating surface on the pad body for applying on the skin surface.

2. Description of Related Arts

Scientist researches that the planet is gradually getting warmer and warmer due to the greenhouse effect. Accordingly, human beings are sensitive when the environmental temperature changes wherein human beings are easy to feel tired and moody via the rapid change of temperature. Therefore, people would like to use a climate control device, such as air-conditioning device or heater, to keep the room at a pleasure temperature. However, such climate control device is considered as an energy exchanging machine that will speed up the process of the greenhouse effect, which is one of the global warning signals.

A climate control pad is an alternative mode of the climate control device to keep the skin surface temperature of the human being at a pleasure temperature. Accordingly, the climate control pad is categorized into two types which are a treatment pad and a seat pad.

Treatment pads are commonly used for relieving muscle pain and enhancing blood circulation. Generally, there are two types of treatment pad, which are cold pad and heat treatment pad. The cold pad is mainly used for decreasing a temperature on the treating skin surface to lower the sensitivity of the nervous system around the treating skin surface. The heat treatment pad is mainly used for increasing a temperature on the treating skin surface to enhance the blood circulation around the treating skin surface.

Accordingly, a conventional seat pad generally comprises a pad body having an air channel provided thereon and an air supplying device connected to the pad body for supplying an air to pass through the air channel, as shown in FIG. 1A. Therefore, when the air supplying device supplies a flow of hot air to circulate within the air channel, the surface of the pad body is warmed up gradually. Likewise, the surface of the pad body becomes cooler when a cool air is supplied via the air supplying device.

The air supplying device is considered as an energy exchanging device to effectively heat up or cool down the air within the air channel in a circulating manner. However, the environmental temperature will be increased via the operation of the air supplying device. In addition, the operating cost of the air supplying device is expensive as if operating an air conditioning device or a heater.

As shown in FIG. 1B, an alternative seat pad generally comprises a pad body, a cushion layer attached on the pad body, and a heating element, such as a heating wire, disposed between the pad body and the cushion layer in such a manner that when the pad body is applied on the skin surface, the heat generated by the heating element is transferred to the skin surface through the cushion layer. However, the climate control pad has several drawbacks.

In order to enhance the thermal conduction of the climate control pad, the cushion layer should minimize its thickness such that the heat from the heating element can effectively pass through the cushion layer to the skin surface. However, when a pressure is applied on the cushion layer, especially when the climate control pad is embodied as a seat pad for a weight of a user applying thereon, the user may substantially feel the heating wire. In other words, the comfortability decreases when a thinner cushion layer is used.

However, when a thicker cushion layer is used for enhancing the comfortability of the climate control pad, the thermal conduction of the climate control pad will be reduced because the heat from the heating element is substantially blocked by the cushion layer. As a result, there is a conflict between comfortability and the thermal conduction of the climate control pad.

In addition, when the heating wire of the heating element is used, the heating wire can only generate the heat in a radial direction so as to directly heat up the surface of the pad body. When the climate control pad is applied on the skin surface, the user can feel the heat around certain areas of the climate control pad where the heating wire is positioned therearound. In other words, the structure of the pad body cannot effectively incorporate with the heating wire to evenly dispense the heat from the heating wire to the contacting surface of the pad body. Therefore, the climate control pad cannot provide an even climate treating surface on the cushion layer to enhance the heat treatment purpose of the climate control pad.

Moreover, since certain heat energy generated from the heating element is blocked by the cushion layer, the heating element must require higher voltage to generate more amount of heat in order to compensate the heat loss through the cushion layer and to maintain the temperature of the climate treating surface of the climate control pad. In other words, the heat conservation of the climate control pad is one of the major concerns for saving energy.

SUMMARY OF THE PRESENT INVENTION

A main object of the present invention is to provide a low voltage and high performance climate control pad for a skin surface, wherein an air circulating circuit is formed on a pad body for a heat generating element disposing thereon so as to provide an even climate treating surface on the pad body for applying on the skin surface.

Another object of the present invention is to provide a low voltage and high performance climate control pad for the skin surface, wherein the air circulating circuit is capable of enhancing the comfortability and the thermal conduction of the climate control pad.

Another object of the present invention is to provide a low voltage and high performance climate control pad for the skin surface, wherein the heat generating element is a safe non-metallic heating material that is soft, flexible, safe and durable. The heat generating element not only has low Electrical Magnetic Interference and complies with CE and UL safety but also provides Far Infrared heat transfer of up to 98.9% with low power consumption. Thus, the heat generating element provides hours of warm and comfortable heat with convenient alkaline batteries or Ni-MH rechargeable batteries.

Another object of the present invention is to provide a low voltage and high performance climate control pad, wherein the air circulating circuit includes an air circulating channel integrally indented on the pad body for receiving the heat generating element therein and a plurality of air conducting grooves communicating with the air circulating channel to guide the heat to evenly disperse on the climate treating surface of the pad body.

Another object of the present invention is to provide a low voltage and high performance climate control pad for the skin surface, wherein the heat generated by the heat generating element heats up the air within the air circulating circuit and maintains therewithin, so as to enhance the heat conservation of the climate control pad. In other words, the present invention is adapted to minimize the heat loss of the heat generating element.

Another object of the present invention is to provide a low voltage and high performance climate control pad for the skin surface, wherein when a cooling source is incorporated with the climate control pad for providing a cooling air through the air circulating circuit, the climate control pad becomes a cold pad for cold treatment purpose. It is worth to mention that the cooling source is embodied as a heat generating element to control the air temperature within the air circulating circuit.

Another object of the present invention is to provide a low voltage and high performance climate control pad for the skin surface, wherein the climate control pad is adapted to function as a seat pad for supporting the user's body thereon so as to provide a cold/hot treating surface for enhancing the comfortability for the user.

Another object of the present invention is to provide a low voltage and high performance climate control pad for the skin surface, which comprises a climate switch to selectively operate the heat generating element for providing the climate treating surface and the cooling source for providing the cool treating surface.

Another object of the present invention is to provide a low voltage and high performance climate control pad for the skin surface, wherein no expensive or complicated structure is required to employ in the present invention in order to achieve the above mentioned objects. Therefore, the present invention successfully provides an economic and efficient solution not only for providing a comfort contact of the climate control pad for the user but also for providing a better thermal conduction of the climate control pad.

Accordingly, in order to accomplish the above objects, the present invention provides a low voltage and high performance climate control pad for applying on a skin surface, comprising:

a power source;

a pad body having a climate treating surface and an air circulating circuit formed thereon for preserving a volume of air within the air circulating circuit in a circulating manner; and a heat generating element which is disposed in the air circulating circuit and electrically connected to the power source, wherein the heat generating element is arranged for generating heat to increase a temperature of the air within the air circulating circuit so as to evenly distribute the heat from the heat generating element on the climate treating surface of the pad body;

wherein the air circulating circuit includes an air circulating channel integrally indented on the pad body for receiving the heat generating element therein and a plurality of air conducting grooves communicating with the air circulating channel to guide the heat to evenly disperse on the climate treating surface of the pad body.

These and other objectives, features, and advantages of the present invention will become apparent from the following detailed description, the accompanying drawings, and the appended claims.

BRIEF DESCRIPTION OF THE DRAWINGS

FIG. 2 is an exploded perspective view of a climate control pad according to a first preferred embodiment of the present invention.

DETAILED DESCRIPTION OF THE PREFERRED EMBODIMENT

Figure 1A:
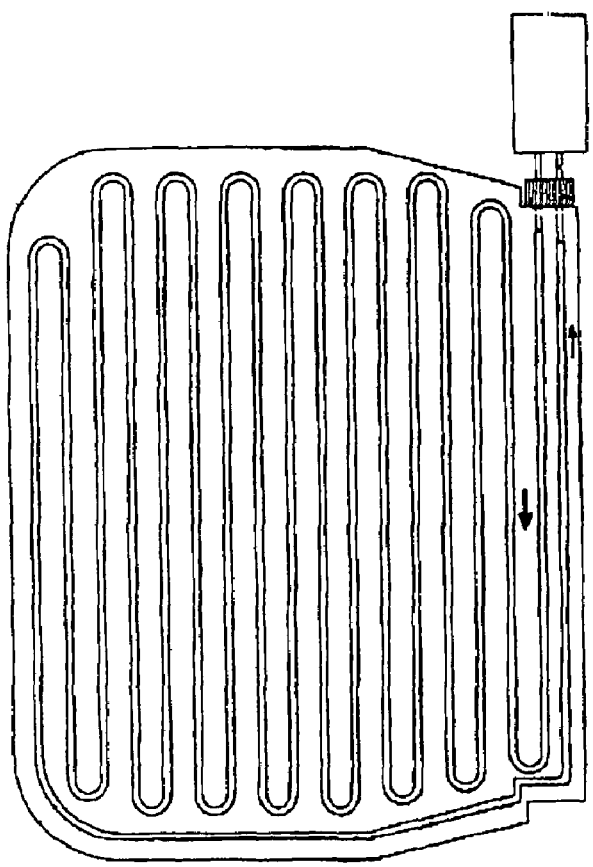
FIGS. 1A and 1B illustrate a convention climate control pad.
Figure 1B:
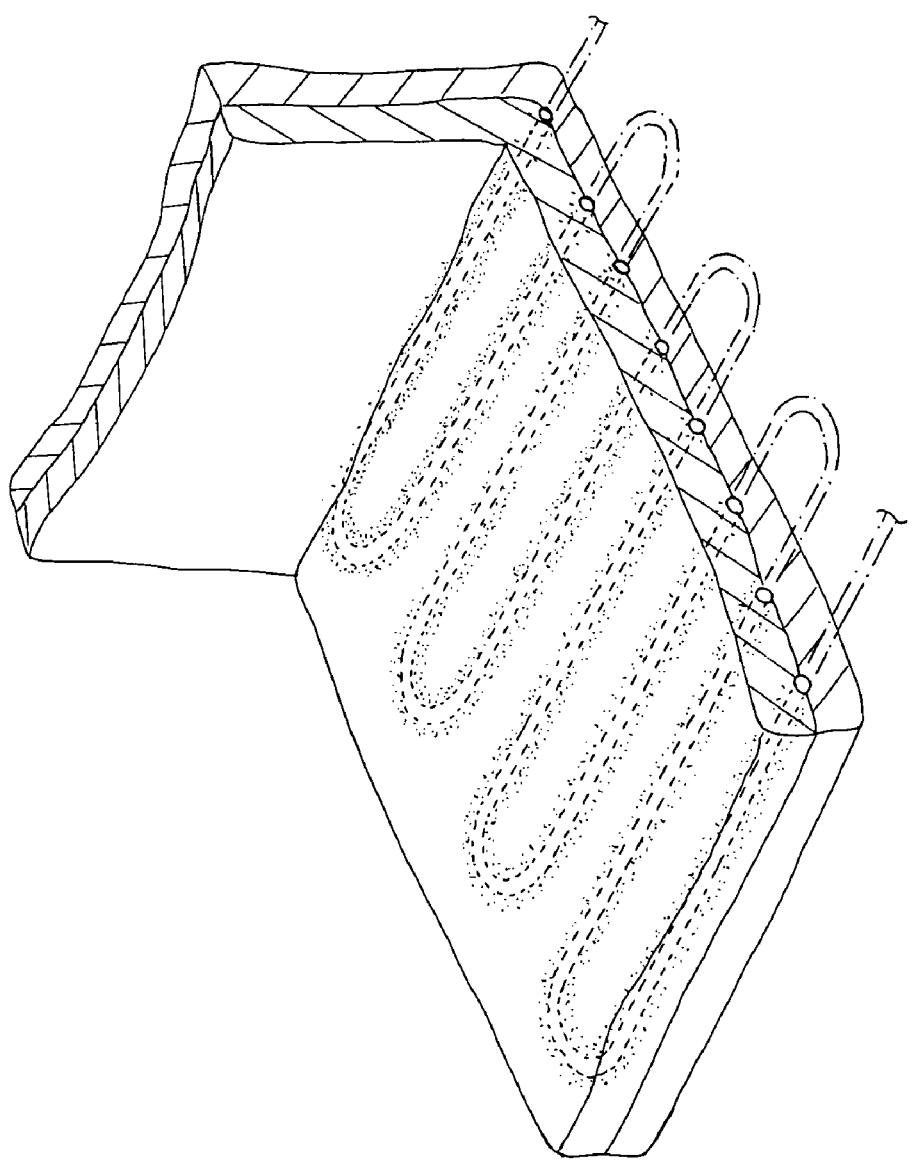
Figure 3:
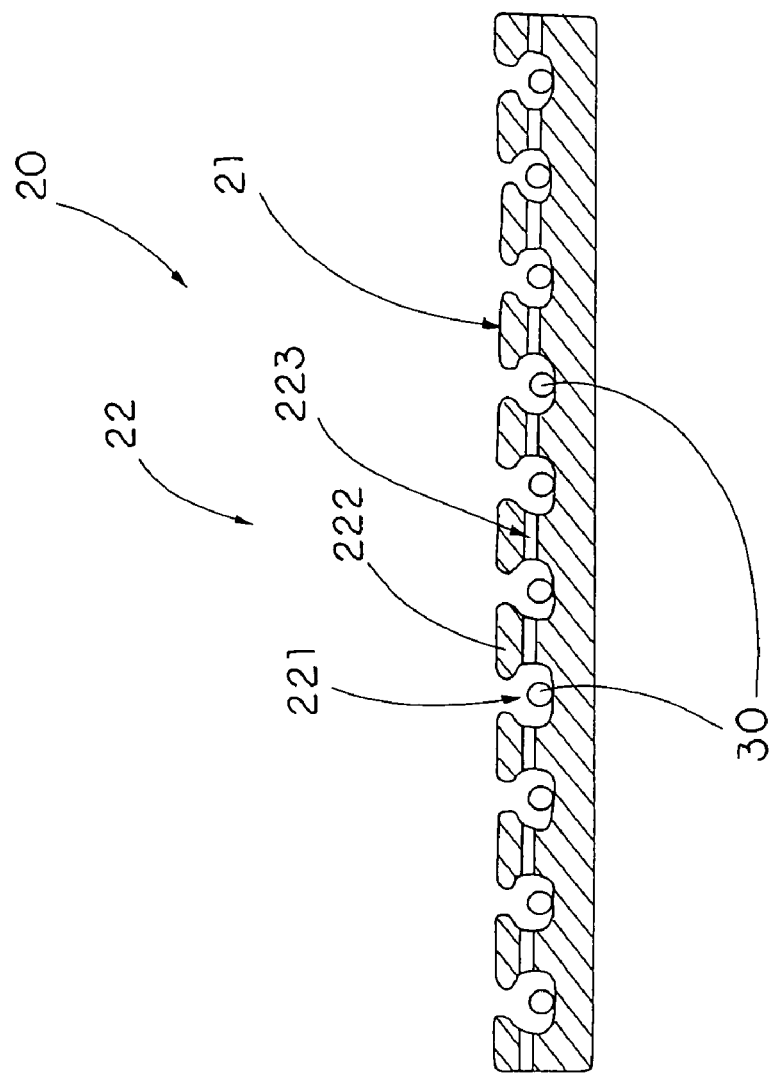
FIG. 3 is a sectional view of the climate control pad according to the above first preferred embodiment of the present invention.

Referring to FIGS. 2 and 3 of the drawings, a climate control pad for applying on a skin surface according to a first preferred embodiment of the present invention is illustrated, wherein the climate control pad comprises a power source 10 and a pad body 20 having a climate treating surface 21 and an air circulating circuit 22 formed thereon for preserving a volume of air within the air circulating circuit 22 in a circulating manner.

The climate control pad further comprises a heat generating element 30 which is disposed in the air circulating circuit 22 and electrically connected to the power source 10, wherein the heat generating element 30 is arranged for generating heat to increase a temperature of the air within the air circulating circuit 22 so as to evenly distribute the heat from the heat generating element 30 on the climate treating surface 21 of the pad body 20.

According to the present invention, the pad body 20 is preferably made of deformable material such as EVA, wherein the climate treating surface 21 of the pad body 20 is arranged to apply on the skin surface in such a manner that the heat on the climate treating surface 21 of the pad body 20 is substantially immense in the skin surface.

The pad body 20 of the climate control pad can be constructed as seat pad for a user sitting thereon, especially for the wheelchair user to enhance the blood circulation thereof via the present invention. Accordingly, when the user sits on the climate control pad, a pressure of the user's weight applying on the pad body 20 is capable of enhancing the contact between the climate treating surface 21 of the pad body 20 and the skin surface.

The air circulating circuit 22 has an elongated air circulating channel 221 integrally indented on the pad body 20 to form an integral guiding wall 222 wherein the climate treating surface 21 is provided at a head portion of the guiding wall 222. As shown in FIG. 2, the air circulating channel 221 is integrally extended in a coil manner that continuously extended from an outer edge of the pad body 20 towards a center thereof.

The air circulating circuit 22 further has a plurality of air conducting grooves 223 spacedly and transversely formed on the guiding wall 222 in such a manner that the air within the air circulating channel 221 is capable of passing through the air conducting grooves 223 so as to enhance an air circulation within the air circulating channel 221.

The heat generating element 30, according to the preferred embodiment, comprises an elongated heating wire which is twisted in a corresponding coil manner and is fittedly disposed in the air circulating channel 221, as shown FIG. 3, wherein the heat generating element 30 is arranged to heat up the air within the air circulating channel 221 so as to evenly distribute the heat to the climate treating surface 21 of the pad body 20. It is worth to mention that the air within the air circulating channel 221 is capable of passing therethrough in a circulating manner such that when the air within the air circulating channel 221 is heated up, the warm air is able to flow along the air circulating channel 221 so as to maintain a uniform temperature of the climate treating surface 21 of the pad body 20.

It is worth to mention that the heat generating element 30 is a low voltage fiber heating wire requiring a low current passing therethrough to generate the heat energy so as to heat up the air within the air circulating circuit 22. The heat generating element 30 is unique and is made of safe non-metallic heating material that is soft, flexible, safe and durable. The heat generating element 30 has low Electrical Magnetic Interference and complies with CE and UL safety. The heat generating element 30 provides Far Infrared heat transfer of up to 98.9% with low power consumption. Thus, the heat generating element 30 provides hours of warm and comfortable heat with convenient alkaline batteries or Ni-MH rechargeable batteries.

It is worth to mention that air is one of the insulating materials so that when the air is heated up by the heat generating element 30, the air within the air circulating channel 222 becomes an insulating layer to conserve the heat therewithin. In addition, the heat generating element 30 can be a conventional heating wire disposed in the air circulating circuit 22 because the heat from the heat generating element 30 can be evenly dispensed to the climate treating surface 21 of the pad body through the air circulating channel 221.

Figure 4:
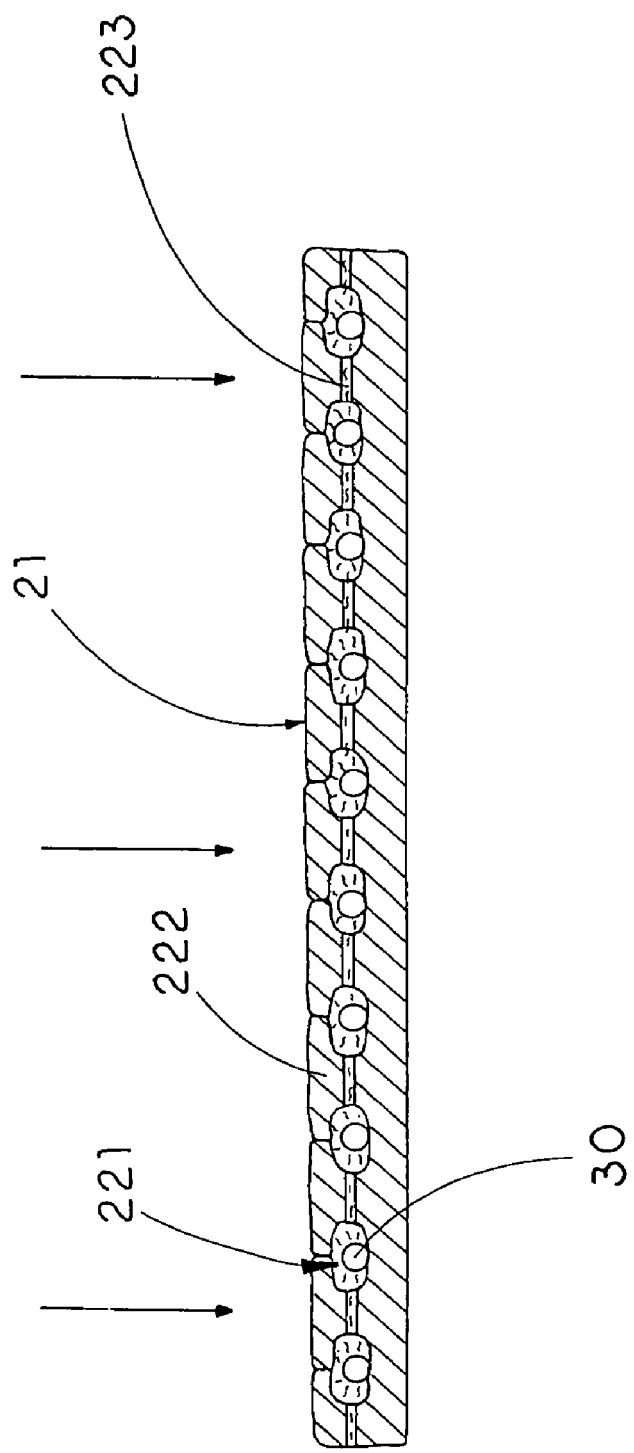
FIG. 4 is a sectional view of the climate control pad according to the above first preferred embodiment of the present invention, illustrating a downward force applying on the pad body to enclose the air circulating circuit.

The head portion of the guiding wall 222 is made of deformable material that is capable of being deformed to enlarge a size thereof when a force is applied on the climate treating surface 21 of the pad body 20 so as to enclose the air circulating channel 221 for retaining the air within the air circulating channel 221 in a circulating manner, as shown in FIG. 4.

In other words, when a downward force of the user's weight is applied on the pad body 20, the head portion of the guiding wall 22 is deformed to enclose the air circulating channel 221 so as to conserve the heat within the air circulating channel. In addition, the foam made guiding wall 222 provides a soft support for the user for enhancing the comfortability of the climate control pad. Therefore, the present invention not only provides a comfort contact of the climate control pad for the user but also provides a better thermal conduction of the climate control pad.

According to the preferred embodiment, the power source 10 is embodied as a power adapter adapted for electrically converting both AC and DC currents to an optimum electric power to the heat generating element 30 in such a manner that the power source 10 is adapted for using both AC current supplied by normal power outlet and DC current supplied by a battery.

Moreover, the climate control pad further comprises a temperature controller 40 electrically connected to the power source 10 for adjustably controlling the temperature of the air within the air circulating channel 222, wherein the temperature controller 40 comprises a heat sensor 41 disposed in the air circulating channel 222 for detecting the temperature therewithin and a current controller 42 electrically connected to the power source 10 for selectively adjusting a current passing through the heat generating element 30.

Therefore, the user is able to select the desired temperature of the climate treating surface 21 of the pad body 20. In other words, the user can preset the temperature of the climate treating surface 21 of the pad body 20 such that when the heat sensor 42 detects the temperature of the air is higher than the preset temperature, the current controller 42 automatically cuts off the current passing to the heat generating element 30 since the heat generating element 30 generates heat when the current passes therethrough. It is worth to mention that when the climate control pad of the present invention incorporates with a cooling source for providing cooling air flowing through the air circulating channel 222 so that the temperature of the air within the air circulating channel 222 is cooled down. Therefore, the present invention is capable of functioning as a cold pad once the climate control pad is incorporated with the cooling source.

Figure 5:
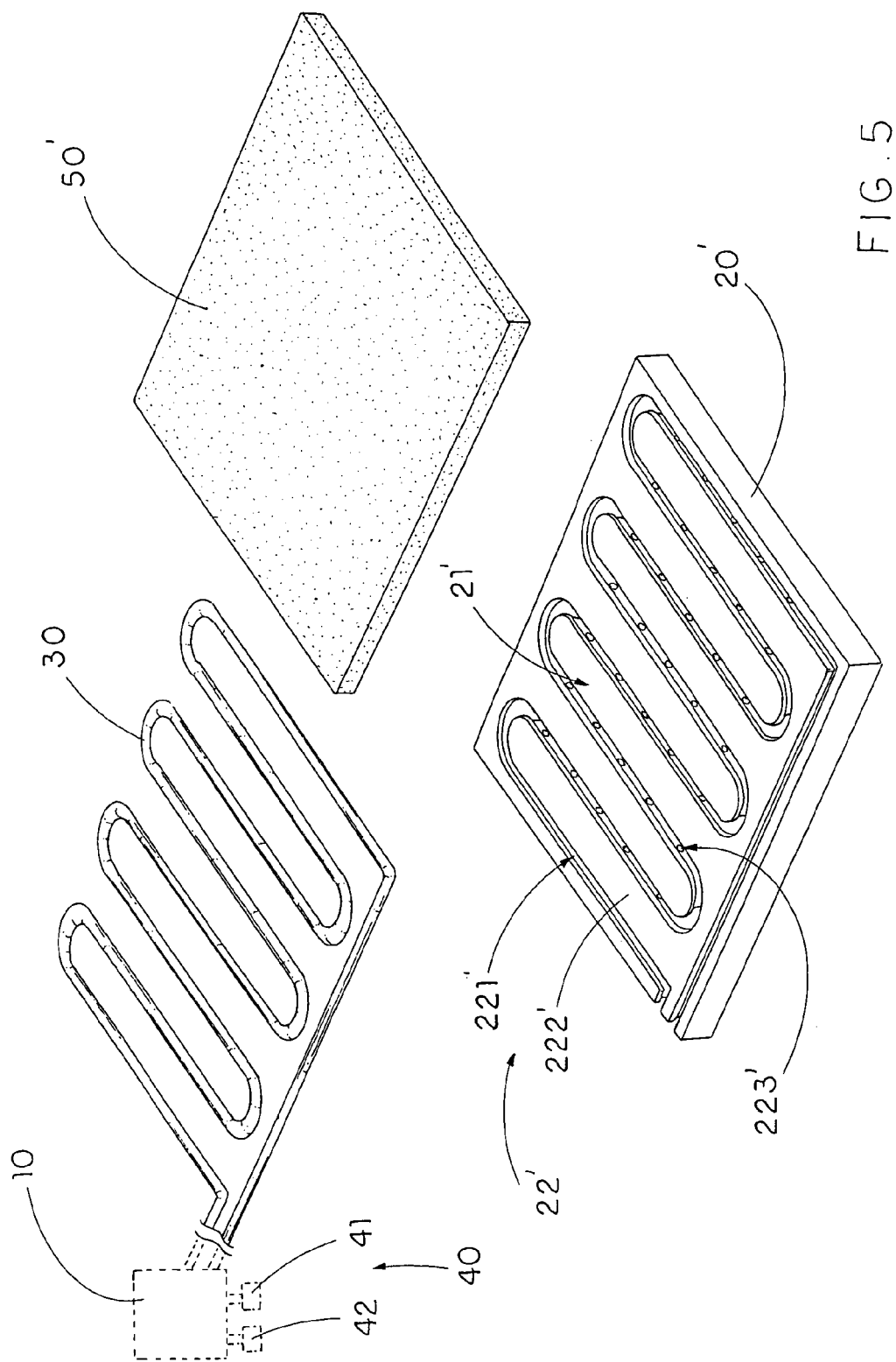
FIG. 5 illustrates a first alternative mode of the pad body of the climate control pad according to the above first preferred embodiment of the present invention.

FIG. 5 illustrates a first alternative mode of the pad body 20' which is made of semi-rigid material such as plastic wherein the air circulating circuit 22' has an elongated air circulating channel 221' integrally indented on the pad body 20' to form an integral guiding wall 222'. The climate treating surface 21' is provided at a head portion of the guiding wall 222' wherein the air circulating channel 221' is integrally extended in a snake-liked manner that continuously extended from one side edge of the pad body 20' to an opposed side edge thereof.

It is worth to mention that the shape of the air circulating channel 221' formed on the pad body 20' is mainly used for fitting the heat generating element 30 therein such that when the heat generating element 30 is bent in a coil manner, the air circulating channel 221' should be shaped to extend on the pad body 20' in a corresponding coil manner for the heat generating element 30 disposing therein.

The climate control pad further comprises a cushion layer 50' overlappedly provided on the climate treating surface 21' of the pad body 20' for providing a soft and comfort contact when the pad body 20' is applied on the skin surface. Since the guiding wall 222' is made of semi-rigid material, the user may feel uncomfortable when the pad body 20' is applied on the skin surface. It is worth to mention that the cushion layer 50' has an air diffusion ability for the air passing therethrough in such a manner that the air heated up within the air circulating channel 221' is capable of diffusing through the cushion layer 50' to the skin surface of the user. Therefore, the cushion layer 50' not only provides a soft comfort feeling when the pad body 20' is applied on the skin surface but also encloses the air circulating channel 221' for conserving the heat of the air therewithin so as to allow the air flowing along the air circulating channel 221' and the air conducting grooves 223' for better air circulation.

However, when the pad body 20 is made of foam material as it is mentioned above in the first embodiment, the cushion layer 50' is still able to provide on the climate treating surface 21' of the pad body 20' so as to further enhance the comfortability of the pad body 20'.

Figure 6:
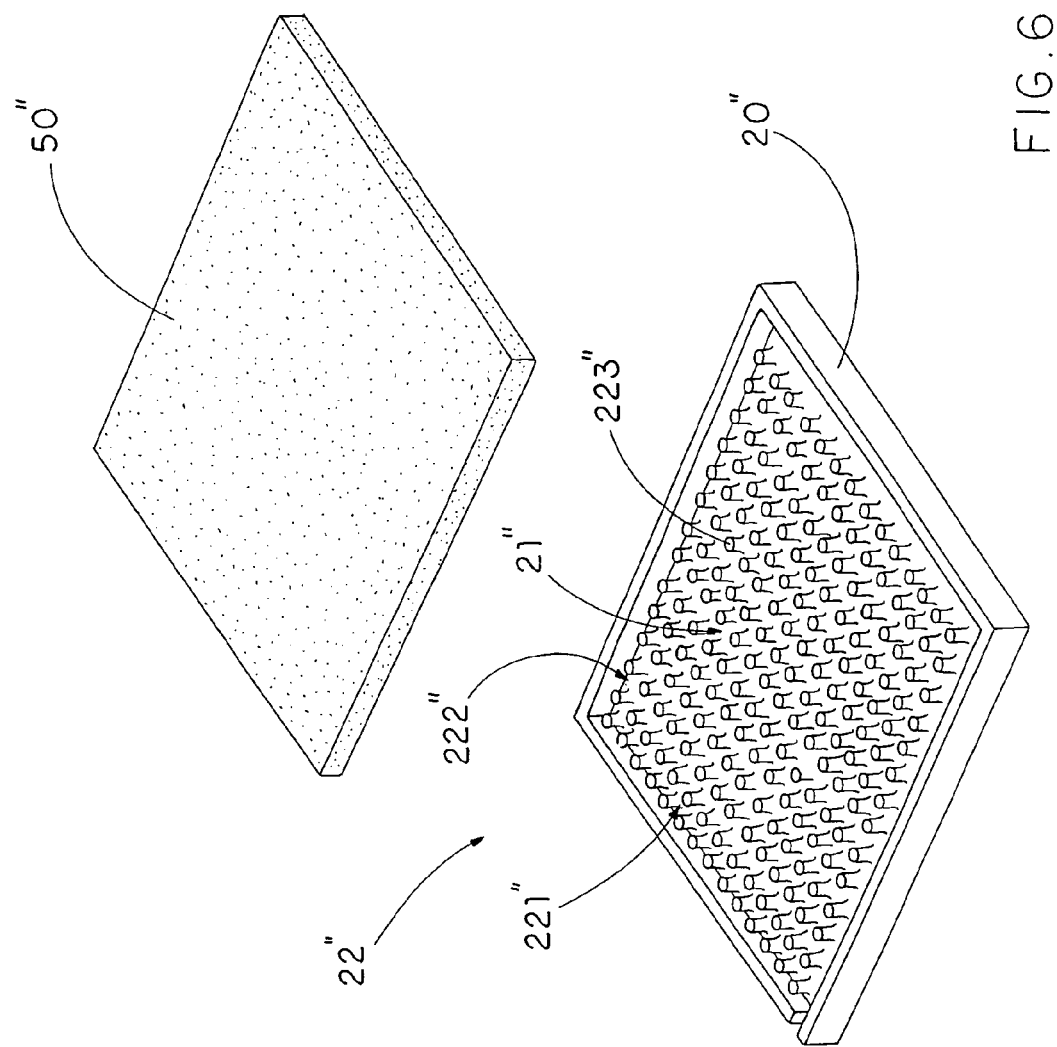
FIG. 6 illustrates a second alternative mode of the pad body of the climate control pad according to the above first preferred embodiment of the present invention.

FIG. 6 illustrates a second alternative mode of the pad body 20" wherein the air circulating circuit 22" has a plurality of longitudinal air circulating channel 221" spacedly indented on the pad body 20" and a plurality of transverse air circulating channel 222" spacedly indented on the pad body 20" to across the longitudinal air circulating channel 221". In other words, the pad body 20" comprises a plurality of rod-liked protrusions 223" evenly and upwardly extending to form the longitudinal air circulating channels 221" and the transverse air circulating channels 222" across the pad body 20", wherein the climate treating surface 21" is formed on head portions of the protrusions 223".

The air circulating circuit 22" is designed as a universal circuit adapted for fittedly disposing the heat generating element 30 therein. In other words, the coil-like or the snake-liked heat generating element 30 is capable of fitting into the longitudinal and transverse air circulating channels 221", 222" so that no pre-shape of the air circulating circuit 22" is required.

Moreover, the air within the air circulating circuit 22" is allowed to be circulated since the intersections between the longitudinal air circulating channels 221" and the transverse air circulating channels 222" provide air spaces for the air passing therethrough, so as to enhance the air circulation of the air circulating circuit 22".

In addition, the climate control pad further comprises a cushion layer 50" overlappedly provided on the climate treating surface 21" of the pad body 20" for providing a soft and comfort contact when the pad body 20" is applied on the skin surface. The cushion layer 50" is adapted to enclose the longitudinal and transverse air circulating channels 221", 222" so that the air heated up by the heat generating element 30 is enclosed with the longitudinal and transverse air circulating channels 221", 222" for heat conservation. It is worth to mention that the cushion layer 50" has air diffusion ability for the air passing therethrough in such a manner that the air heated up within the air circulating channel 221" is capable of diffusing through the cushion layer 50" to the skin surface of the user.

Figure 7:
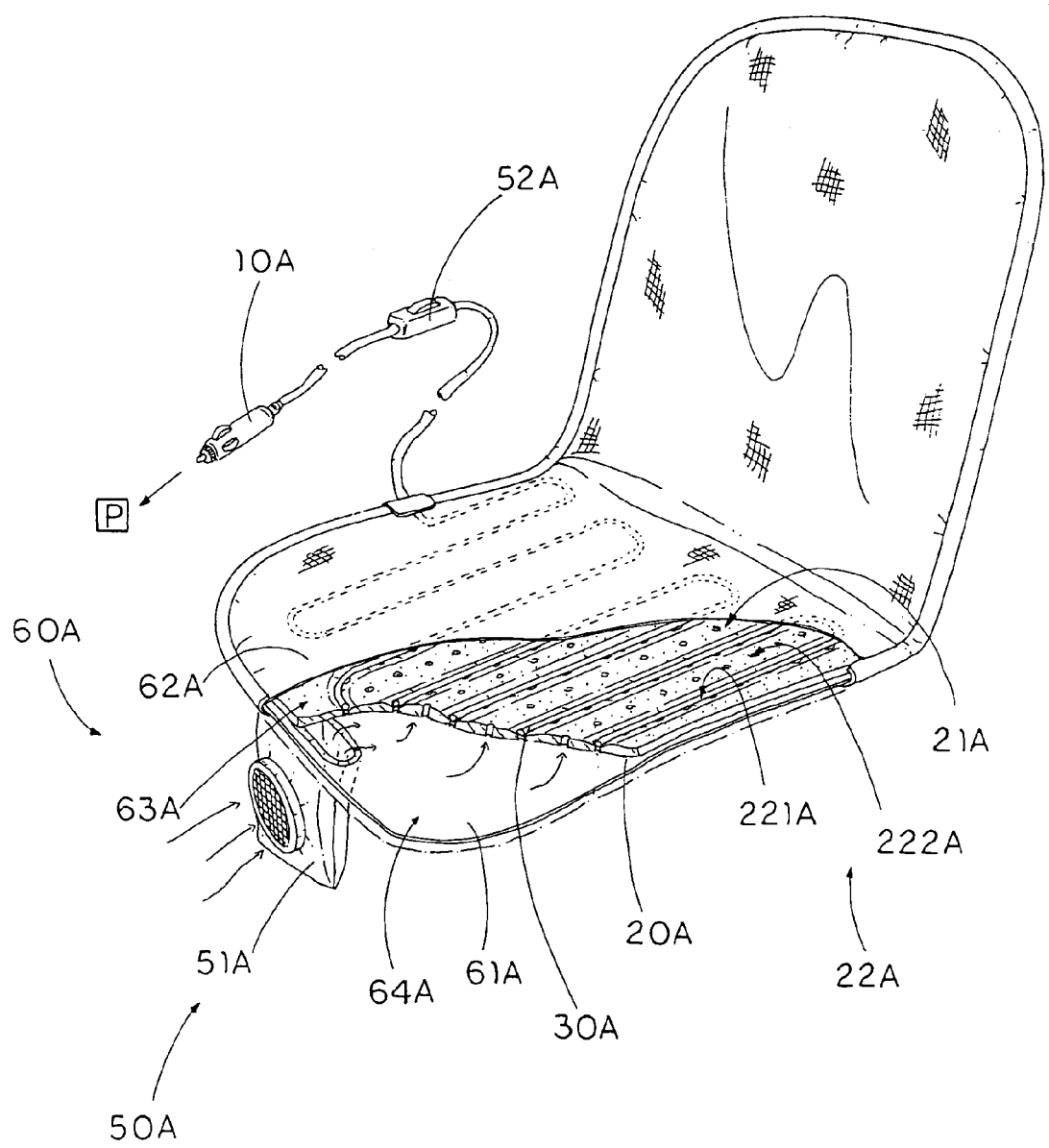
FIG. 7 is a sectional perspective view of a climate control pad according to a second preferred embodiment of the present invention.

As shown in FIG. 7, a climate control pad of a second embodiment illustrates an alternative mode of the first embodiment of the present invention, wherein the climate control pad 20A having a climate treating surface 21A and an air circulating circuit 22A formed thereon, and a heat generating element 30A which is disposed in the air circulating circuit 22A and electrically connected to the power source 10A for generating heat to increase the temperature of the air within the air circulating circuit 22A.

The air circulating circuit 22A has an elongated circulating channel 221A integrally indented on the pad body 20A in a snake-liked manner that continuously extended from one side edge of the pad body 20A to an opposed side edge thereof wherein the heat generating element 30A comprise a low voltage fiber heating wire which is twisted in a corresponding snake-liked manner and is fittedly disposed in the air circulating channel 221A. It is worth to mention that the heat generating element 30, 30A according to the first and second embodiments and their alternatives, is a low voltage fiber heating wire requiring a low current passing therethrough to generate the heat energy so as to heat up the air within the air circulating circuit 22, 22', 22", 22A.

As shown in FIG. 7, the climate control pad further comprises an air sucking device 50A electrically connected to the power source 10A for sucking an external air towards a bottom side of the pad body 20A, wherein the pad body 20A has a plurality of air passages 222A evenly extended from the climate treating surface 21A of the pad body 20A to the bottom side thereof through the air circulating channel 221A for guiding the external air evenly flowing to the climate treating surface 21A of the pad body 20A.

It is worth to mention that when the air within the air circulating channel 221A is heated up via the heat generating element 30A, the flow of the external air will mix with the air within the air circulating channel 221A and will evenly release at the climate treating surface 21A of the pad body 20A so as to provide an even climate treating surface for the user.

Accordingly, the air sucking device 50A comprises a sucking fan 51A having an air inlet for sucking the external air from the air inlet towards the bottom side of the pad body 20A, and a control switch 52A electrically connected the sucking fan 51A with the heat generating element 30A for selectively operating the heat generating element 30A in an on and off manner while the sucking fan 51A is switched on. Therefore, the user is able to switch on the sucking fan 51A while the heat generating element 30A is switched off for letting the external air passing to the climate treating surface 21A of the pad body 20A as a cooling surface thereof. Likewise, when both the sucking fan 51A and the heat generating element 30A are switched on via the control switch 52A, the external air is mixed with the heated air within the air circulating channel 221A to flow to the climate treating surface 21A of pad body 20A as an even heat treatment for the user. It is worth to mention that the control switch 52A is sidewardly extended from the pad body 20A for facilitating the practical use of the climate control pad of the present invention.

As shown in FIG. 7, the climate control pad of the present invention is embodied as a car seat pad adapted for placing on a car seat of a vehicle, wherein the control switch 52A is electrically connected to the power source 10A for electrically connecting to a power supply of the vehicle.

The climate control pad further comprises a pad pocket 60A having a bottom air insulating layer 61A and a top air diffusion layer 62A overlapped on the air insulating layer 61A to define a storage cavity 63A therebetween for receiving the pad body 20A within the storage cavity 63A, wherein an air receiving cavity 64A is formed between the bottom side of the pad body 20A and the air insulating layer 61A for receiving the external air from the air sucking device 50A so as to reinforce the external air flowing towards the climate treating surface 21A of the pad body 20A.

In view of above, the present invention, according to the first and second embodiments and their alternatives, requires lower voltage in comparison with the conventional climate control pad since the air insulation layer is formed for heat transfer. Also, the heat generated by the heat generating element 30, 30A is used for heating up the air within the air circulating circuit 22, 22', 22" 22A to evenly distribute on the climate treating surface 21, 21', 21", 21A of the pad body 20, 20', 20", 20A. Therefore, the climate control pad of the present invention provides high performance heat conservation that the heat is evenly spread over the entire climate treating surface 21, 21', 22", 21A.

One skilled in the art will understand that the embodiment of the present invention as shown in the drawings and described above is exemplary only and not intended to be limiting.

It will thus be seen that the objects of the present invention have been fully and effectively accomplished. The first and second embodiments and their alternatives have been shown and described for the purposes of illustrating the functional and structural principles of the present invention and is subject to change without departure from such principles. Therefore, this invention includes all modifications encompassed within the spirit and scope of the following claims.

What is claimed is:

1. A climate control pad for applying on a skin surface, comprising:

a power source;

a pad body having a climate treating surface and an air circulating circuit formed thereon for preserving a volume of air within said air circulating circuit in a circulating manner; and a heat generating element which is disposed in said air circulating circuit and electrically connected to said power source, wherein said heat generating element is arranged for generating heat to increase a temperature of said air within said air circulating circuit so as to evenly distribute said heat from said heat generating element on said climate treating surface of said pad body;

wherein said air circulating circuit has an elongated air circulating channel integrally indented on said pad body to form an integral guiding wall, wherein said climate treating surface is provided at a head portion of said guiding wall;

wherein said head portion of said guiding wall is made of deformable material that is capable of being deformed to enlarged a size thereof when a force is applied on said climate treating surface of said pad body so as to enclose said air circulating channel for retaining said air within said air circulating channel in a circulating manner.

2. A climate control pad for applying on a skin surface, comprising:

a power source;

a pad body having a climate treating surface and an air circulating circuit formed thereon for preserving a volume of air within said air circulating circuit in a circulating manner; and a heat generating element which is disposed in said air circulating circuit and electrically connected to said power source, wherein said heat generating element is arranged for generating heat to increase a temperature of said air within said air circulating circuit so as to evenly distribute said heat from said heat generating element on said climate treating surface of said pad body;

wherein said air circulating circuit has an elongated air circulating channel integrally indented on said pad body to form an integral guiding wall, wherein said climate treating surface is provided at a head portion of said guiding wall;

wherein said air circulating circuit further has a plurality of air conducting grooves spacedly and transversely formed on said guiding wall in such a manner that said air circulating channel is allowed to pass through said air conducting grooves so as to enhance an air circulation within said air circulating channel.

3. The climate control pad, as recited in claim 1, wherein said air circulating circuit further has a plurality of air conducting grooves spacedly and transversely formed on said guiding wall in such a manner that said air circulating channel is allowed to pass through said air conducting grooves so as to enhance an air circulation within said air circulating channel.

4. The climate control pad, as recited in claim 3, wherein said heat generating element is a low voltage fiber heating wire that requires a low current passing therethrough for generating said heat to heat up said air within said air circulating circuit.

5. The climate control pad, as recited in claim 4, wherein said air circulating channel is integrally extended in a coil manner that continuously extended from an outer edge of said pad body towards a center thereof, wherein said heat generating element comprises an elongated heating wire which is twisted in a corresponding coil manner and is fittedly disposed in said air circulating channel.

6. The climate control pad, as recited in claim 4, wherein said air circulating channel is integrally extended in a snake-liked manner that continuously extended from one side edge of said pad body to an opposed side edge thereof, wherein said heat generating element comprises an elongated heating wire which is twisted in a corresponding snake-liked manner and is fittedly disposed in said air circulating channel.

7. The climate control pad, as recited in claim 3, further comprising a temperature controller electrically connected to said power source for adjustably controlling said temperature of said air within said air circulating channel, wherein said temperature controller comprises a heat sensor disposed in said air circulating channel for detecting said temperature therewithin and a current controller electrically connected to said power source for selectively adjusting a current passing through said heat generating element.

8. The climate control pad, as recited in claim 4, further comprising a temperature controller electrically connected to said power source for adjustably controlling said temperature of said air within said air circulating channel, wherein said temperature controller comprises a heat sensor disposed in said air circulating channel for detecting said temperature therewithin and a current controller electrically connected to said power source for selectively adjusting a current passing through said heat generating element.

9. A climate control pad for applying on a skin surface, comprising:

a power source;

a pad body having a climate treating surface and an air circulating circuit formed thereon for preserving a volume of air within said air circulating circuit in a circulating manner; and a heat generating element which is disposed in said air circulating circuit and electrically connected to said power source, wherein said heat generating element is arranged for generating heat to increase a temperature of said air within said air circulating circuit so as to evenly distribute said heat from said heat generating element on said climate treating surface of said pad body;

wherein said air circulating circuit has an elongated air circulating channel integrally indented on said pad body to form an integral guiding wall, wherein said climate treating surface is provided at a head portion of said guiding wall;

wherein said climate control pad further comprises an air sucking device electrically connected to said power source for sucking an external air towards a bottom side of said pad body, wherein said pad body further has a plurality of air passages evenly formed on said climate treating surface of said pad to said bottom side thereof through said air circulating channel for guiding said external air evenly flowing to said climate treating surface of said pad body.

10. The climate control pad, as recited in claim 9, wherein said air sucking device comprises a sucking fan for sucking said external air towards said bottom side of said pad body, and a control switch electrically said sucking fan with said heat generating element for selectively operating said heat generating element in an on and off manner while said sucking fan is switch on.

11. The climate control pad, as recited in claim 9, further comprising a pad pocket having a bottom air insulating layer and a top air diffusion layer overlapped on said air insulating layer to define a storage cavity therebetween for receiving said pad body within said storage cavity, wherein an air receiving cavity is formed between said bottom side of said pad body and said air insulating layer for receiving said external air from said air sucking device so as to reinforce said external air flowing towards said climate treating surface of said pad body.

12. The climate control pad, as recited in claim 10, further comprising a pad pocket having a bottom air insulating layer and a top air diffusion layer overlapped on said air insulating layer to define a storage cavity therebetween for receiving said pad body within said storage cavity, wherein an air receiving cavity is formed between said bottom side of said pad body and said air insulating layer for receiving said external air from said air sucking device so as to reinforce said external air flowing towards said climate treating surface of said pad body.

13. The climate control pad, as recited in claim 9, wherein said air circulating channel is integrally extended in a snake-liked manner that continuously extended from one side edge of said pad body to an opposed side edge thereof, wherein said heat generating element comprises a low voltage fiber heating wire which is twisted in a corresponding snake-liked manner and is fittedly disposed in said air circulating channel.

14. The climate control pad, as recited in claim 10, wherein said air circulating channel is integrally extended in a snake-liked manner that continuously extended from one side edge of said pad body to an opposed side edge thereof, wherein said heat generating element comprises a low voltage fiber heating wire which is twisted in a corresponding snake-liked manner and is fittedly disposed in said air circulating channel.

15. The climate control pad, as recited in claim 12, wherein said air circulating channel is integrally extended in a snake-liked manner that continuously extended from one side edge of said pad body to an opposed side edge thereof, wherein said heat generating element comprises a low voltage fiber heating wire which is twisted in a corresponding snake-liked manner and is fittedly disposed in said air circulating channel.

* * * * *